United States Patent
Kang et al.

(10) Patent No.: US 6,324,894 B1
(45) Date of Patent: Dec. 4, 2001

(54) DEVICE AND METHOD FOR MEASURING ARGON IMPURITY BY UTILIZING THE TRIPLE POINT AND THE γ-β TRANSITION TEMPERATURES OF OXYGEN

(75) Inventors: Kee-Hoon Kang; Chang-Ho Song; Yong-Gyoo Kim; Kee-Sool Gam, all of Daejeon (KR)

(73) Assignee: Korea Research Institute of Standards and Science, Daejeon (KR)

(*) Notice: Subject to any disclaimer, the term of this patent is extended or adjusted under 35 U.S.C. 154(b) by 0 days.

(21) Appl. No.: 09/301,158

(22) Filed: Apr. 28, 1999

(30) Foreign Application Priority Data

May 25, 1998 (KR) .................................................. 98-18905

(51) Int. Cl.[7] .............................. G01N 25/18; F25J 3/00; G01K 11/00
(52) U.S. Cl. ..................... 73/25.03; 73/25.01; 73/31.01; 62/639; 62/924; 374/159
(58) Field of Search ................................ 73/31.01, 31.02, 73/31.03, 25.01, 25.03; 374/45, 159; 62/637, 924

(56) References Cited

U.S. PATENT DOCUMENTS 4,451,273 * 5/1984 Cheng et al. .......................... 62/637

FOREIGN PATENT DOCUMENTS

54157669-A * 12/1979 (JP) ...................................... 73/25.03

OTHER PUBLICATIONS

Journal of Research of the National Bureau of Standards, vol. 91, No. 5, "The Triple Point of Oxygen in Sealed Transportable Cells", Furukawa, pp. 255–275, Sep.–Oct. 1986.
Advances in Cryogenic Engineering, vol. 33, "Evidence of Unreliability of Factory Analysis", Pavese et al., pp. 1039–1043, Jan. 1988.

* cited by examiner

Primary Examiner—Hezron Williams
Assistant Examiner—Michael Cygan
(74) Attorney, Agent, or Firm—Finnegan Henderson Farabow Garrett & Dunner LLP (57) ABSTRACT

The present invention relates to a quantitative measuring method of argon impurity contained in high purity oxygen by means of triple point and γ-β phase transition of oxygen, and also to a cryostat employed in quantitative measuring of argon impurity contained in high purity oxygen.

3 Claims, 5 Drawing Sheets

DEVICE AND METHOD FOR MEASURING ARGON IMPURITY BY UTILIZING THE TRIPLE POINT AND THE γ-β TRANSITION TEMPERATURES OF OXYGEN

BACKGROUND OF THE INVENTION

1. Field of the Invention

The present invention relates to a quantitative measuring method of argon impurity contained in high purity oxygen and cryostat employed in the above method and more particularly, to a quantitative measuring method of argon impurity by means of a triple point and a temperature at γ-β phase transition of the high purity oxygen and cryostat employed in the above method.

2. Description of the Prior Art

Generally, a purity of the high purity oxygen is determined by quantitative analysis of impurity using chemical analysis method. Currently, the high purity oxygen having the purity of 99.998% is commonly used.

The conventional chemical analysis method is usually performed by a mass measurement method using gas mass apparatus. And in this case, the chemical analysis apparatus using mass difference of an ionized gas, etc. measures a content of the impurity accurately.

However, because oxygen and argon have similar chemical properties (polarity, etc.), the signals of both gases are overlapped in case of using the conventional analysis method. Hence, the conventional analysis has a decisive shortcoming that a content of argon impurity is not accurately measured. Accordingly, it is required to provide a more accurate measurement method of argon impurity contained in high purity oxygen. And for the purpose of measuring argon impurity accurately, the signal of oxygen should be separated from that of argon.

SUMMARY OF THE INVENTION

In order to solve the aforementioned problem, the inventor et al have conducted intensive studies on the method of measuring argon impurity contained in high purity oxygen employing triple point and γ-β phase transition of oxygen and as a result, completed this invention.

Accordingly, it is a primary object of the present invention to provide a quantitative measuring method of argon impurity contained in high purity oxygen by means of triple point and γ-β phase transition of oxygen.

It is a further object of the present invention to provide a cryostat employed for quantitative measuring of argon impurity contained in high purity oxygen.

DESCRIPTION OF THE DRAWINGS

The accompanying drawings, which are incorporated in and constitute a part of the specification, illustrate an embodiment of the invention, and, together with the description, serve to explain the principles of the invention:

FIG. 4b is graphical representation showing replotted solidification curve of FIG. 4a;

FIG. 5b is graphical representation showing replotted solidification curve of FIG. 5a;

DETAILED DESCRIPTION OF THE INVENTION

This invention is characterized by a quantitative measuring method of argon impurity contained in high purity oxygen by means of triple point and γ-β phase transition of oxygen, comprising the steps of:

(i) measuring the contents of impurity in high purity sample except argon impurity using conventional chemical analysis method;

(ii) freezing and melting of the high purity sample and standard sample whose impurity is predetermined;

(iii) measuring the triple points of the samples based on the ratio of melting which results from the step (ii);

(iv) measuring the temperature at γ-β phase transition of the samples preceded by decreasing the temperature of the samples; and (v) measuring the quantities of the argon impurity by comparing the triple point and the temperature at γ-β phase transition of the high purity sample with those of standard sample.

Also, this invention is characterized by a cryostat employed in quantitative measuring of argon impurity contained in high purity oxygen, which comprises:

(i) a closed vacuum can (10) which can be opened or closed, having vacuum pump (11);

(ii) first and second radiation shield cans (20a,20b) mounted in the inner of the vacuum can (10);

(iii) a sample cell (30) mounted as closed state in the inner of the first radiation shield can (20a) for receiving sample from the outer of the vacuum can (10); and (iv) a thermometer pocket (31) and heater (32) mounted around the sample cell (30).

This invention is explained in more detail as set forth hereunder:

The quantitative measuring method according to this invention is characterized in that the method uses triple point and temperature at γ-β phase transition of oxygen. This method comprises the steps of (i) measuring the contents of impurity in high purity sample except argon impurity using conventional chemical analysis method; (ii) freezing and melting of the high purity sample and standard sample whose impurity is predetermined; (iii) measuring the triple points of the samples based on the ratio of melting which results from the step (ii); (iv) measuring the temperature at γ-β phase transition of the samples preceded by decreasing the temperature of the samples; and (v) measuring the quantities of the argon impurity by comparing the triple point and the temperature at γ-β phase transition of the high purity sample with those of standard sample.

Also, the step of (ii) may be performed by melting and freezing the sample at least two times and then slowly freezing again. The separated solidification curve is obtained through the step. And, it is preferred that the slow freezing has the cooling rate lower than 40 mK/min.

The cryostat according to this invention comprises: (i) a closed vacuum can (10) which can be opened or closed, having vacuum pump (11); (ii) first and second radiation shield cans (20a,20b) mounted in the inner of the vacuum can (10); (iii) a sample cell (30) mounted as closed state in the inner of the first radiation shield can (20a) for receiving sample from the outer of the vacuum can (10); and (iv) a thermometer pocket (31) and heater (32) mounted around the sample cell (30).

Figure 1:
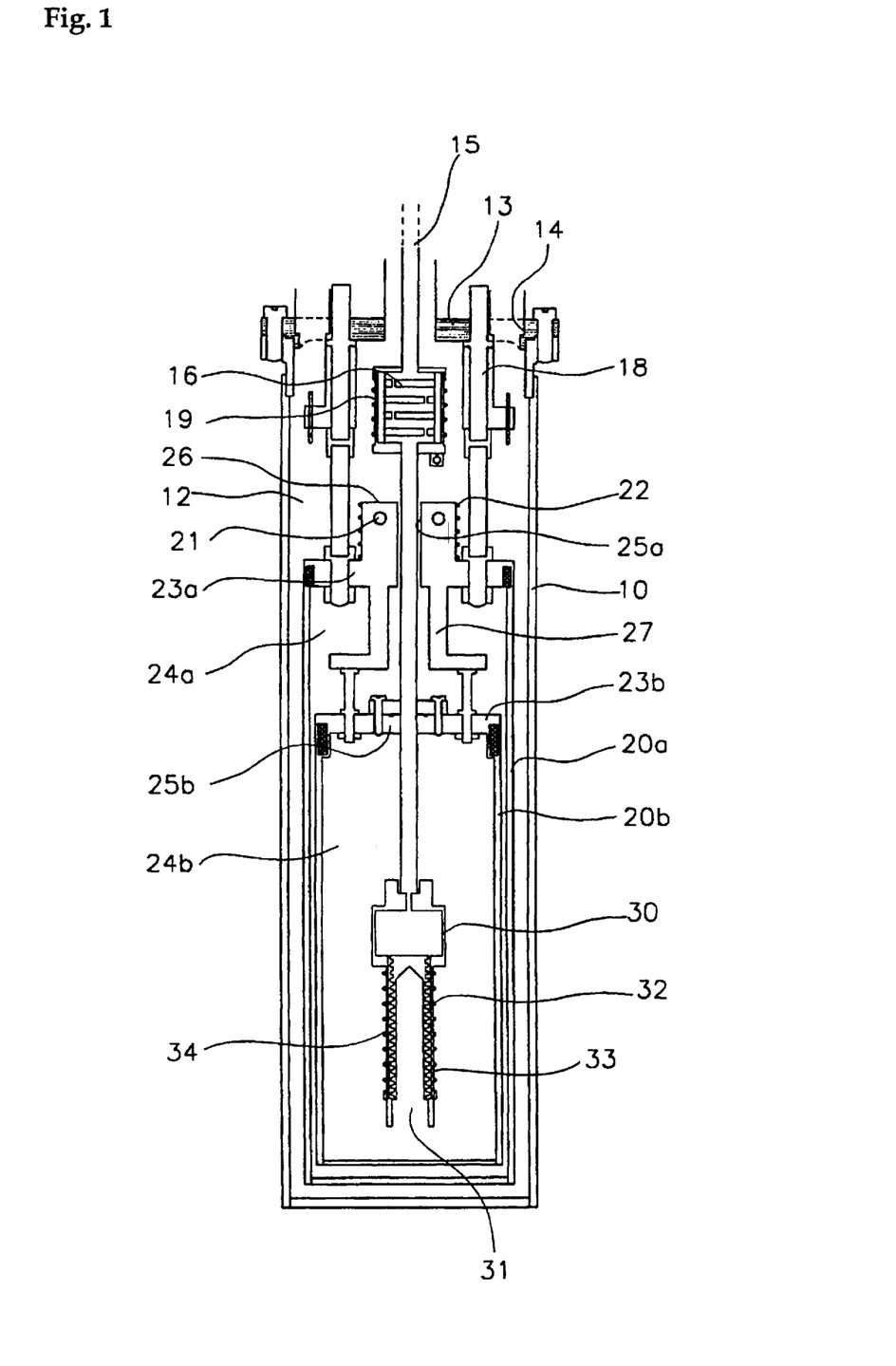
FIG. 1 is sectional view of a cryostat that can measure accurately content of impurity in high purity oxygen according to the present invention.

The cryostat according to this invention is explained in more with accompanying Fig. as follows:

FIG. 1 shows sectional view of the cryostat according to the present invention. In FIG. 1, reference number 10 denote vacuum can, and reference number 11 denote vacuum pump (be not shown).

The vacuum can (10), made of material enduring prescribed pressure, is hollow vessel and located in the outermost of the cryostat.

Particularly, a space (12) with defined size is formed in the inner of the vacuum can (10), and a cover (13) for opening and closing is mounted in the upper of the vacuum can (10).

The cover prevents the space (12) from being exposed to the external.

The mounting hole (14) is formed through the upper side of the cover (13), and the vacuum pump (11) (be not shown) is mounted in the mounting hole (14).

So, the inner of the space (12) is evaporated by the vacuum pump (11), thereby minimizing heat loss due to convection between the sample cell (30) mounted in the vacuum can (10) and the outer of vacuum can (10).

According to this invention, it is preferred that the sample cell (30) comprise the gas inlet tube (15) with the heat exchanger (16). The gas inlet tube (15) is inserted in the upper side center of the cover (13) so as to inject sample into sample cell (30).

Further, the gas inlet tube (15) is connected with sample cell (30) and has a function of injecting the sample, received from the outer of vacuum can (10), into the sample cell (30).

The gas inlet tube (15) is supported at the lower of the cover (13) in order to pass through heat exchanger (16) between the second radiation shield can (20b). When the sample flows into the gas inlet tube (15), an influx heat from the exterior is transferred into the vacuum can (10).

In one preferred mode of the present invention, the heat exchanger (16) has a heater (19) for exchanging heat and said transferred heat through the gas inlet tube (15) is so efficiently exchanged in the space (12).

Preferably, the vacuum can (10) comprises the copper pole (18) for exchanging heat generated in sample cell (30) due to cooling sample with outer of the vacuum can (10) through the first and the second radiation shield cans (20a, 20b).

One end of the copper pole (18) is mounted in the cover (13) and the other end of that is mounted in the cover (23) so as to hang the second radiation shield can (20b). So, the second radiation shield can (20b) hung by the other end of the copper pole (18), does not come in contact with bottom of the space (12). Also, the copper pole (18) prevents heat generated in the terminals for temperature measurement and of heater from transferring into the sample cell (30).

The space (24a, 24b) of the radiation shield cans (20a, 20b) is smaller than that of vacuum can (10).

Particularly, since the size of the first radiation shield can (20a) is smaller than that of the second radiation shield can (20b), the first radiation shield can (20a) is inserted into the second radiation shield can (20b).

The copper blocks (23a, 23b) which is openable, are mounted in the radiation shield cans (20a, 20b) respectively. Also, penetrated holes (25a, 25b) are formed in the center of the copper blocks (23a, 23b), respectively so that the gas inlet tube (15) may insert into the inner of the radiation shield cans (20a, 20b).

At the part approximating to penetrated hole (25b) of the upper side of the copper block (23b), a projecting part (26) is formed upward.

Preferably, the second radiation shield can (20b) comprises thermometer pocket (21) and heater (22), which are employed for controlling heat conducted from the outer of the vacuum can (10)

The thermometer pocket (21) and heater (22) are mounted in the projecting part (26). As mentioned above, the first radiation shield can (20a) is mounted in the other end (lower end) of the copper pole (18) and suspended in vacuum can (10).

Also, the second radiation shield can (20b) is suspended in supporting bracket (27) which is formed as one body in the lower of the copper block (23b).

The second radiation shield can (20b) is constructed to exchange heat in the vacuum can (10). In like manner, the first radiation shield can (20a) is constructed to exchange heat with the second radiation shield can (20b).

Reference number 30 denotes the sample cell.

The sample cell (30) is filled with the sample having high purity so as to measure content of impurity, and mounted in lower end of gas inlet tube (15) which is inserted in the inner of the radiation shield cans (20a, 20b).

A cylindrical part (33) is downward formed in the lower of the sample cell (30), and the heater (32) is mounted in the circumference side of the cylindrical part (33).

A resistance thermometer is perpendicularly mounted in the center of the cylindrical part (33) and measures internal temperature of the sample cell (30).

Then, the sample cell (30) is filled with the sample through the gas inlet tube (15) and the sample repeatedly is frozen and melted by means of heat exchange.

In preferred embodiment of the present invention, the sample cell (30) in a volume of 7.5 cm³ is utilized.

When the triple point temperature and the temperature at the γ-β phase transition of solid oxygen is measured, the sample is charged to about 80–90% of the sample cell volume in proportion to the total volume. Also, when impurities in the sample is measured, the sample is charged to 1.3 cm³ of the sample cell in proportion to the total volume.

The quantitative measuring method and the operation of the cryostat according to the present invention is explained with reference to the accompanying FIG. 2 to FIG. 6 as follows:

Prior to applying the processing of this invention, variety and content of impurity in a standard sample are accurately measured till 0.1 ppm using the conventional chemical analysis method. Also, impurity except argon in a measurement sample is measured by the chemical analysis method. Then, the high purity measurement sample is injected in sample cell (30) through the gas inlet tube (15), and then the temperature of the cryostat is lowered by the method of heat exchange so that the temperature of the measurement sample may be lowered below freezing point.

In this condition, as internal pressure of the sample cell is lowered slowly, the measurement sample in gas state is condensed. With time, the temperature of the measurement sample is lowered below freezing point and is instantaneously raised till coexistence temperature of liquid and solid, after which the sample is supercooled.

When the supercooled sample is more cooled, liquid in the sample cell (30) is transited to solid state and the temperature of liquid is dropped again.

Then, the frozen sample is repeatedly melted at a fixed rate (e.g., 5–10%) by means of heater (32) in the sample cell (30). The temperature at every moment when the sample is melted, is measured by resistance thermometer in the cylindrical part (33).

Preferably, the resistance thermometer utilizes the platinum-resistance thermometer with a thermometer bridge having above 0.000001 Ω of resistance resolution. Therefore, triple point curve is obtained from resistance temperature change of the sample melted at a defined rate.

The following specific examples are intended to be illustrative of the invention and should not be construed as limiting the scope of the invention as defined by appended claims.

EXAMPLE 1

Figure 2:
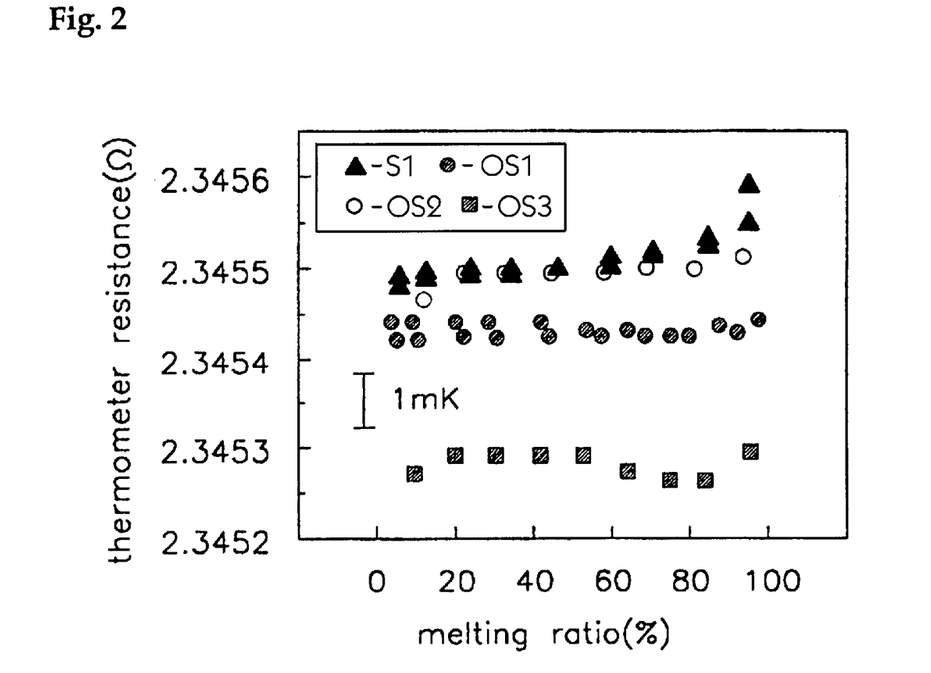
FIG. 2 is graphical representation showing triple point temperature change of common used high purity oxygen (hereunder, referred to as "S1"); a oxygen sample prepared in the laboratory (hereunder, referred to as "OS1"); a oxygen sample consisting of argon impurity and the above prepared oxygen sample (hereunder, referred to as "OS2"); and a oxygen sample consisting of nitrogen impurity and the above prepared oxygen sample (hereunder, referred to as "OS3")

FIG. 2 shows each triple point change of four samples. Marking (▲) represents standard sample (hereunder, referred to as "S1") with 99.997% of purity having impurity content as recorded in the following Table. 1 which is measured by conventional chemical analysis method.

And, marking (●) represents measurement sample (hereunder, referred to as "OS1") which is made in such a manner that $KMnO_4$ is heated and decomposed; marking (○) represents samples (hereunder, referred to as "OS2") made in such a manner that argon 100 ppm of purity 99.9995% is added in OS1; marking (■) represents samples (hereunder, referred to as "OS3") made in such a manner that nitrogen 100 ppm of purity 99.9995% is added in OS1.

TABLE 1

Standard sample with 99.997% of purity

| Impurity | Content (ppm) |
| --- | --- |
| Argon | Below 5 |
| Nitrogen | 5 |
| Methane | 0.1 |
| Carbon dioxide | 0.1 |
| Nitrogen oxide | 0.1 |
| Krypton | 1 |
| Xenon | 1 |
| Hydrogen | 1 |
| Helium | 1 |
| Water | 1.6 |

Compared with each triple point temperature in FIG. 2, it was known that triple point temperature of the OS2 containing 100 ppm of argon was higher than that of the measurement sample, and triple point temperature of the OS3 containing 100 ppm of nitrogen was lower than that of the measurement sample.

Then, resistance difference which was measured by platinum-resistance thermometer was converted into temperature, and average value of the converted temperature was calculated. The triple point temperature of the OS2 was higher 0.94 mK (9.4 μK/ppm) than that of the OS1 but that of the OS3 was lower 2.08 mK (20.8 μK/ppm) than that of the measurement sample, and triple point temperature of the S1 was higher 1.08 mK than that of the measurement sample.

That is, triple point temperature of high purity material containing impurity was usually lowered; however, the triple point temperature of high purity oxygen containing argon as impurity was risen.

It will apparently be known that the consequence related to the difference of the triple point temperature is well agreed with contents of following literatures: (i) F. Pavese, D. Ferri and D. Giraudi, Evidence of Unreliability of Factory Analyses of Argon Impurity in Oxygen, *BIPM Com. Thermometrie*, Document CCT/87-48(1987); (ii) Cryogenic Engineering and G. t. Furnkawa, The Triple Point of Oxygen In Sealed Transportable Cell, *J. Res. Natl. Bur. Stand.*, 91(5), 225–275(1986).

If the OS1 has the highest purity of the samples, it may be considered that the S1 has argon impurity more than 100 ppm in comparison with OS1. If the S1 has the highest purity of the samples, it may be considered that the OS1 contains about 50 ppm of nitrogen impurity.

Further, while temperature difference between the OS1 and the OS3 was 2.08 mK (20.8 μK/ppm), temperature difference between the S1 and the OS1 was 1.08 mK. Therefore, the impurity of S1 was a half of that of the OS3. That is, it will be recognized that the OS1 has nitrogen impurity of about 50 ppm.

EXAMPLE 2

Figure 3:
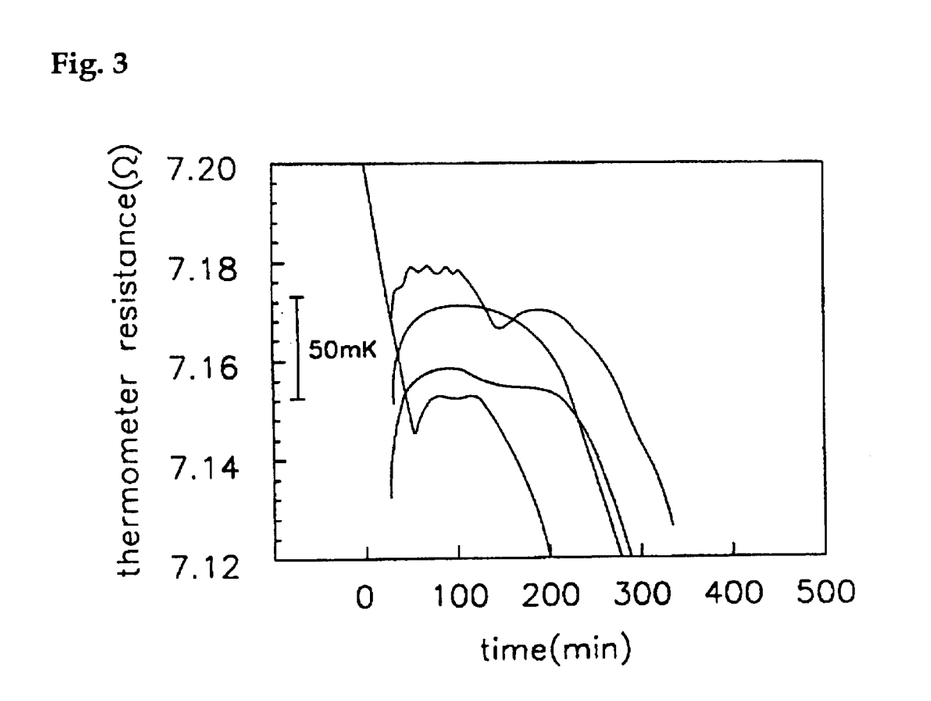
FIG. 3 is graphical representation showing the temperature change at γ-β phase transition of the samples described in FIG. 2.

FIG. 3 shows the temperature change at γ-β phase transition of the samples of Example 1.

Using the cryostat, the oxygen samples of FIG. 2 was cooled below freezing point so that phase transition was generated. At the beginning, crystal structure of the solid oxygen samples were shown to cubical γ phase. Then, the temperatures of them were lowered below 43.7964K, and so crystal structure of the solid oxygen was transited to face centered cubic β phase. Consequently, γ-β phase transition was generated.

Though the temperature at γ-β phase transition of oxygen sample was generally varied with kind and content of impurity, it is practically lowered in proportion to content of impurity as shown in FIG. 3.

Compared with the highest temperature at phase transition of the oxygen samples, the temperature of OS1 was higher 18 mK (180 μK/ppm) and 52 mK (520 μK/ppm), respectively, than that of the OS2 and the OS3.

Judging from the temperature difference, it will be recognized that temperature change between the OS1 and the OS2 is 18 mK per argon 100 ppm, and between the OS1 and the OS3, it is 52 mK per nitrogen 100 ppm.

It will be recognized that impurity content calculated from the value of temperature change is very similar to that calculated from the value of the triple point temperature variation as described above. Particularly, the measurement of argon impurity using the temperature at γ-β phase transition is nineteen times as accurate as that using the triple point and in case of nitrogen impurity, it is twenty-five times.

As a result of fact, triple point temperature of the S1 is higher 1.08 mK than that of the OS1, and the temperature at γ-β phase transition of S1 is lower 68 mK than that of the OS1. And the contents of argon impurity calculated from the temperature changes are 115 ppm and 129 ppm. The content of argon impurity is much more than that of argon impurity recorded in Table. 1 (5 ppm), and therefore it will be appreciated that the method according to this invention has reliability of twenty times than conventional chemical analysis method.

EXAMPLE 3

As mentioned above, although content of argon impurity in the S1 was measured by means of triple point temperature and γ-β phase transition, it was difficult to measure impurity in the OS1 due to the absence of comparable criterion sample.

Therefore, in order to overcome aforementioned problem the present invention provides to a quantitative measuring method by repeating freezing and melting of solid oxygen.

Figure 4A:
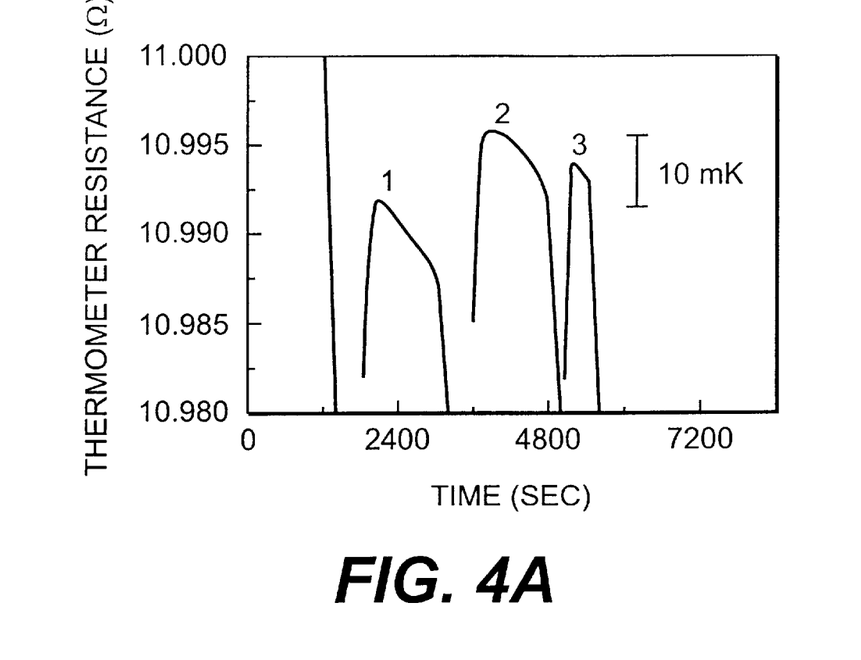
FIG. 4a is graphical representation showing solidification curve of S1 obtained by melting and freezing the sample two times and then slowly freezing again with a cooling rate of 40 mK/min.
Figure 4B:
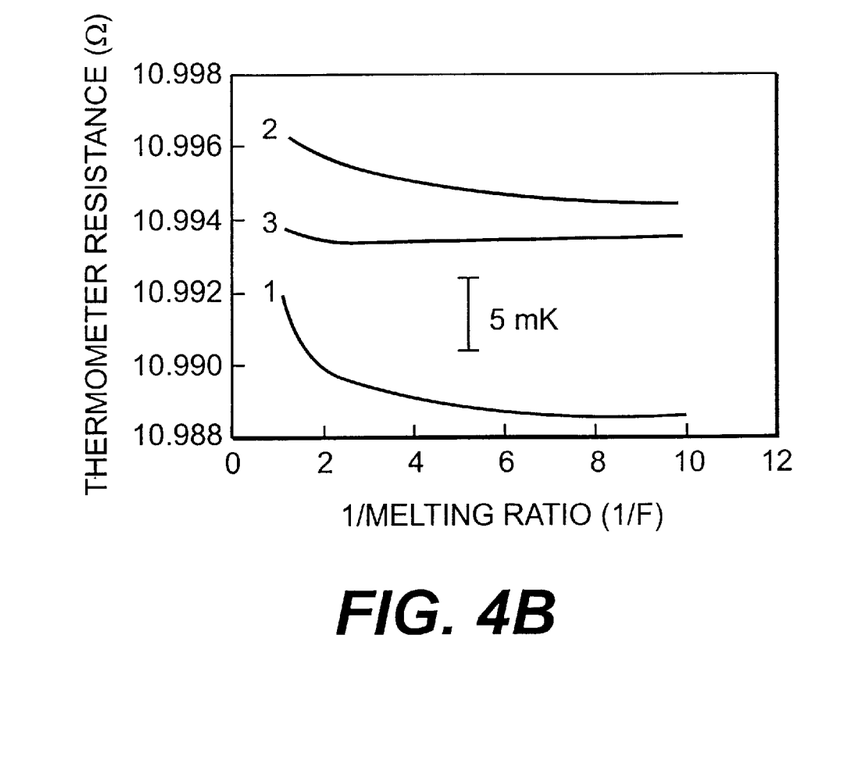
Figure 5A:
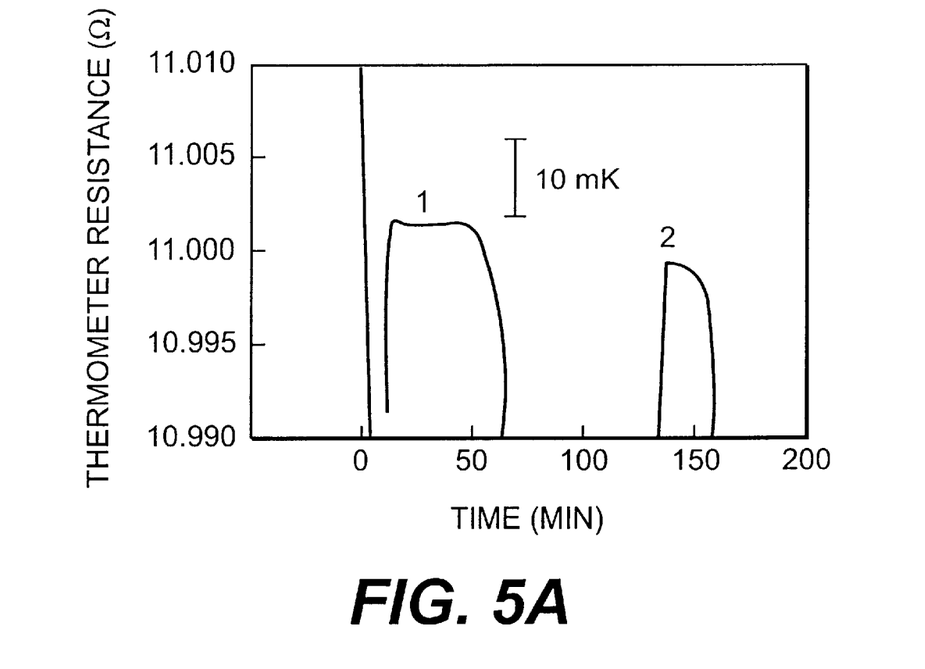
FIG. 5a is graphical representation showing solidification curve of OS1 obtained by melting and freezing the sample two times and then slowly freezing again with a cooling rate of 40 mK/min.
Figure 5B:
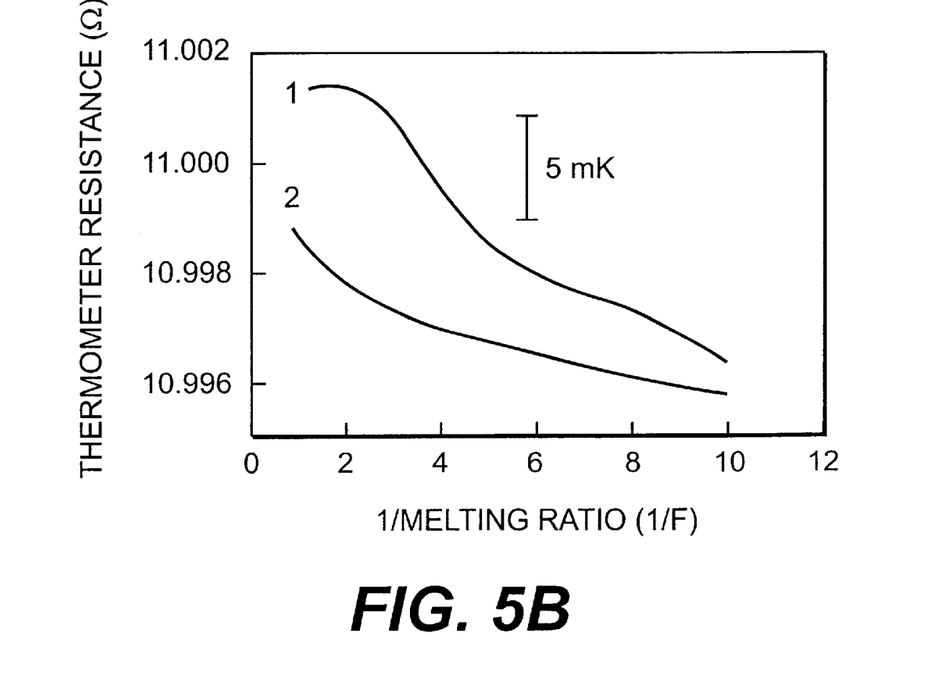

In FIG. 4 and FIG. 5, solidification curve was obtained in such a manner that temperature was lowered with velocity of 40 mK/min, after the sample had been frozen and melted twice.

The reason that the solidification curve, namely, separated curve was obtained, is as follows:

As a liquid sample was frozen slowly, impurity was moved to the solid-liquid interface where solubility between solid and liquid greatly differed; thereby forming interface containing relative high-concentration impurity. Thus, the site of sample where solidification took place at first, had a relatively high purity, and other site of sample where supercooling happened subsequently, had a higher concentration of impurity than the former.

In FIG. 4a, freezing point of curve 1 was lower than that of curve 2 and 3, because the S1 contained more than 100 ppm of the argon impurity as known in FIGS. 2 and 3.

FIG. 4b are graphical representation showing temperature change relative to reciprocal of melting ratio (1/F). In case that the value of 1/F is 1, the difference of temperature between curve 1 and curve 2 is approximately 10 mK. The difference value of 10 mK is ten times than that of triple point. This is because the slow solidification gives rise to concentration of impurity at one side.

In FIG. 5a, freezing point of curve 2 was lower than that of curve 1, because the OS1 contained nitrogen impurity more than argon.

EXAMPLE 4

Figure 6A:
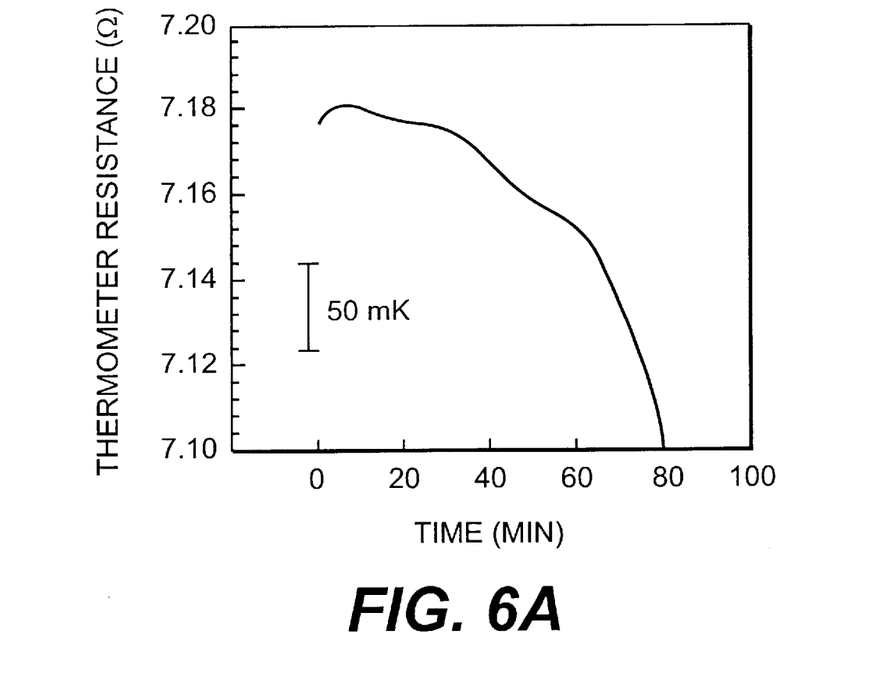
FIG. 6a is graphical representation showing the temperature at γ-β phase transition of OS1 that is frozen at first.
Figure 6B:
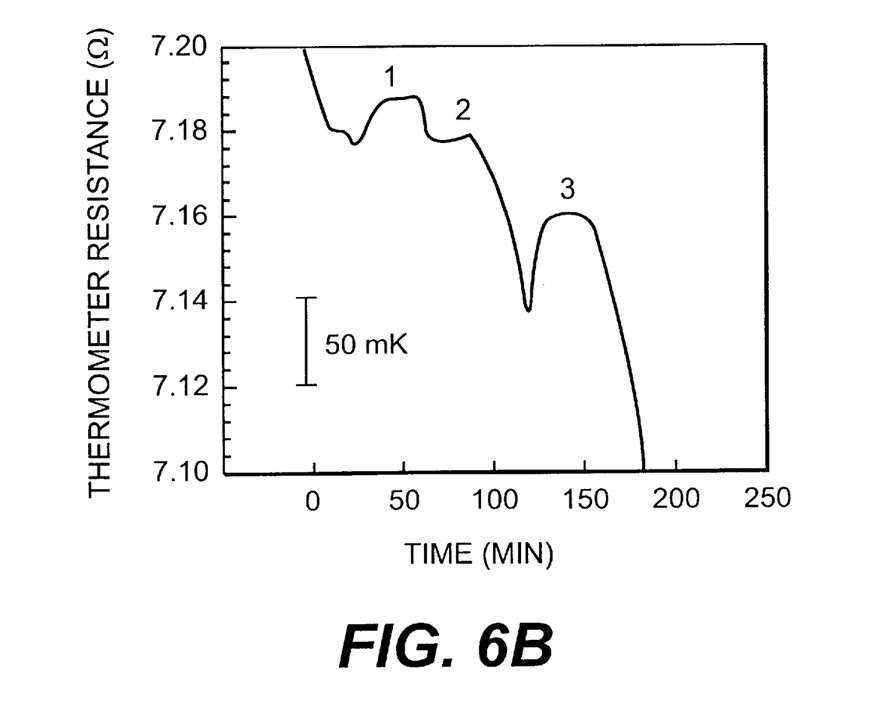
FIG. 6b is graphical representation showing the temperature at γ-β phase transition of OS1 that is obtained through three times melting and freezing treatment.

FIG. 6 is graphical representation showing the temperature at γ-β phase transition of a oxygen sample passed through the treatment of FIG. 4.

More specifically, FIG. 6a is γ-β phase transition curve of the OS1 which is frozen at first in above step. As illustrated in FIG. 6a, the curve was single, because the impurity contained in the sample was evenly distributed.

FIG. 6b is γ-β phase transition curve of the OS1 which is obtained through three times melting and freezing process. As shown in FIG. 6b, the curve had three peaks and the reason for formation of three peak is the same as described in that for separated curve in freezing curve.

While, in FIG. 6a, the thermometer resistance at γ-β phase transition was 7.18 Ω, the curve 1 of FIG. 6b showed more than 7.18 Ω. This is because a part frozen at first is more pure than starting sample.

Also, the temperature difference at γ-β phase transition between curve 3 of FIG. 6b and FIG. 6a was 55 mK. If the temperature difference is due to argon or nitrogen impurity, it corresponds to 106 ppm of argon or 306 ppm of nitrogen. And the impurity value is three-fold concentrated value, the concentration of argon and nitrogen are 33 ppm and 102 ppm, respectively, in case evenly distributed on overall sample.

If the OS1 contains only 102 ppm of nitrogen impurity, the difference of triple point temperature in FIG. 2 between S1 and OS1 is 2.02 mK. The difference, however, is 1.08 mK. And to take the difference value into consideration, it is assumed that the OS1 contains at most 52 ppm of nitrogen and at least 17 ppm of argon. Thus, the OS1 contains nitrogen impurity less than 52 ppm and argon impurity in the range of 17 ppm–35 ppm.

Consequently, if the content of nitrogen impurity in OS1 is quantitatively measured by conventional chemical analysis method, the content of argon impurity is measured by the method of the present invention.

What is claimed is:

1. A quantitative measurement method of argon impurity contained in high-purity oxygen by means of triple point temperature and γ-β phase transition temperature of oxygen, comprising the steps of:
   (i) measuring the contents of impurities in a high-purity sample except argon impurity using a conventional chemical analysis method;
   (ii) freezing and melting the high-purity sample and a standard sample whose impurities are predetermined;
   (iii) measuring the triple point temperatures of the high-purity sample and the standard sample based on a ratio of melting resulted from the step (ii);
   (iv) measuring the temperature of γ-β phase transition of the high-purity sample and the standard sample preceded by decreasing the temperature of the high-purity sample and the standard sample; and
   (v) measuring the quantity of the argon impurity by comparing the triple point temperature and the γ-β phase transition temperature of the high-purity sample with those of the standard sample.

2. The quantitative measurement method of argon impurity according to claim 1, wherein the step (ii) is performed by freezing and melting the high-purity sample and a standard sample at least twice and then slowly freezing the high-purity sample and the standard sample again.

3. The quantitative measurement method of argon impurity according to claim 2, wherein the step of the slowly freezing the high-purity sample and the standard sample is performed at a cooling rate lower than 40 mK/min.

* * * * *

UNITED STATES PATENT AND TRADEMARK OFFICE
CERTIFICATE OF CORRECTION

PATENT NO. : 6,324,894 B1
DATED : December 4, 2001
INVENTOR(S) : Kee-Hoon Kang, Chang-Ho Song, Yong-Gyoo Kim and Kee-Sool Gam It is certified that error appears in the above-identified patent and that said Letters Patent is hereby corrected as shown below:

<u>Title page,</u>
ABSTRACT, should be deleted in its entirety and replaced with:
-- The present invention relates to a device and a method for quantitatively measuring argon impurity contained in high-purity oxygen. More particularly, the present invention relates to a cryostat and its method of use for quantitatively measuring the argon impurity by means of triple point temperature and $\gamma$ - $\beta$ phase transition temperature of the high-purity oxygen. --

Signed and Sealed this

Second Day of July, 2002

*Attest:*

*Attesting Officer*

JAMES E. ROGAN
*Director of the United States Patent and Trademark Office*